United States Patent
Ahn

(10) Patent No.: US 10,842,735 B2
(45) Date of Patent: Nov. 24, 2020

(54) HAIR GROWTH-PROMOTING COMPOSITION

(71) Applicant: Dong Hyun Ahn, Seoul (KR)

(72) Inventor: Dong Hyun Ahn, Seoul (KR)

( * ) Notice: Subject to any disclaimer, the term of this patent is extended or adjusted under 35 U.S.C. 154(b) by 66 days.

(21) Appl. No.: 15/531,340

(22) PCT Filed: Nov. 25, 2015

(86) PCT No.: PCT/KR2015/012708
§ 371 (c)(1),
(2) Date: May 26, 2017

(87) PCT Pub. No.: WO2016/085250
PCT Pub. Date: Jun. 2, 2016

(65) Prior Publication Data
US 2017/0319468 A1    Nov. 9, 2017

(30) Foreign Application Priority Data

Nov. 28, 2014 (KR) .......................... 10-2014-0168236
Sep. 8, 2015 (KR) .......................... 10-2015-0126824

(51) Int. Cl.

| | | |
|---|---|---|
| A61K 8/98 | (2006.01) | |
| A61K 31/164 | (2006.01) | |
| A61K 33/30 | (2006.01) | |
| A61K 35/12 | (2015.01) | |
| A61K 8/42 | (2006.01) | |
| A61K 31/4188 | (2006.01) | |
| A61K 38/18 | (2006.01) | |
| C12N 5/0775 | (2010.01) | |
| A61K 8/27 | (2006.01) | |
| A61K 8/64 | (2006.01) | |
| A61K 8/67 | (2006.01) | |
| A61Q 7/00 | (2006.01) | |
| C12N 5/077 | (2010.01) | |
| A61K 35/28 | (2015.01) | |

(52) U.S. Cl.
CPC ............... *A61K 8/981* (2013.01); *A61K 8/27* (2013.01); *A61K 8/42* (2013.01); *A61K 8/64* (2013.01); *A61K 8/673* (2013.01); *A61K 31/164* (2013.01); *A61K 31/4188* (2013.01); *A61K 33/30* (2013.01); *A61K 35/12* (2013.01); *A61K 38/18* (2013.01); *A61K 38/1808* (2013.01); *A61K 38/1825* (2013.01); *A61K 38/1866* (2013.01); *A61Q 7/00* (2013.01); *C12N 5/0653* (2013.01); *C12N 5/0663* (2013.01); *A61K 35/28* (2013.01); *A61K 2800/78* (2013.01); *A61K 2800/85* (2013.01); *C12N 2500/22* (2013.01); *C12N 2500/38* (2013.01); *C12N 2500/90* (2013.01); *C12N 2501/11* (2013.01); *C12N 2501/115* (2013.01); *C12N 2513/00* (2013.01); *C12N 2533/52* (2013.01); *C12N 2533/54* (2013.01); *C12N 2533/80* (2013.01)

(58) Field of Classification Search
CPC . A61K 8/981; A61K 8/27; A61K 8/42; A61K 8/64; A61K 8/673; A61K 31/164; A61K 31/4188; A61K 33/30; A61K 35/12; A61K 38/18; A61K 38/1808; A61K 38/1825; A61K 38/1866; A61K 35/28; A61K 2800/78; A61K 2800/85; A61Q 7/00; C12N 5/0653; C12N 5/0663; C12N 2500/22; C12N 2500/38; C12N 2500/90; C12N 2501/11; C12N 2501/115; C12N 2513/00; C12N 2533/52; C12N 2533/54; C12N 2533/80
USPC ....................................................... 435/325
See application file for complete search history.

(56) References Cited

U.S. PATENT DOCUMENTS

2007/0077232 A1    4/2007  Naughton et al.

FOREIGN PATENT DOCUMENTS

| KR | 10-2012-0126284 A | 11/2012 |
| KR | 10-1218101 B1 | 1/2013 |
| KR | 10-2013-0103115 A | 9/2013 |
| WO | 2013/167927 A1 | 11/2013 |

OTHER PUBLICATIONS

Huang et al., Adipose-Derived Stem Cells: Isolation, Characterization, and Differentiation Potential, Cell Transplantation, vol. 22, pp. 701-709, 2013.*
Ditucci, What is the difference between D-biotin and Biotin, Livestrong, Accessed Apr. 26, 2019, Available online at: www.livestrong.com/article/156332-what-is-difference-between-d-biotin-and-biotin/.*

* cited by examiner

Primary Examiner — Jennifer M. H. Tichy
(74) Attorney, Agent, or Firm — Novick, Kim & Lee, PLLC; Sang Ho Lee

(57) ABSTRACT

Provided is a hair growth-promoting composition comprising: 100 parts by weight of a stem cell culture solution obtained from a culture medium of mesenchymal stem cells which have been subcultured two or more times; 0.001 to 0.1 parts by weight of zinc; 5 to 50 parts by weight of a panthenol based compound; and 0.0001 to 0.1 parts by weight of a water-soluble vitamin, wherein it is sprayed or applied on the scalp to promote hair growth. Said hair growth-promoting composition may have an excellent effect and improve economical efficiency in treating alopecia due to a simple delivery method of the composition.

3 Claims, 1 Drawing Sheet

HAIR GROWTH-PROMOTING COMPOSITION

TECHNICAL FIELD

The present invention relates to a hair-growth-promoting composition capable of having an excellent hair-growth effect and significantly simplifying a hair growth procedure in an alopecia treatment field.

BACKGROUND ART

Recently, as an interest in beauty has increased, an interest in treating alopecia has also increased. Although hair does not have an important physiological function directly associated with life, the hair has functions of serving as a buffer from external impacts, blocking ultraviolet (UV) light, protecting a human body from external stimulation, and absorbing unnecessary heavy metals such as arsenic, mercury, zinc, and the like, from the human body to discharge these heavy metals to the outside. A growth stage of the hair is classified into an anagen stage in which the hair grows; a catagen stage in which growth stops, and the hair bulb is degraded, thereby causing metabolism to be delayed; and a telogen stage in which the follicles shrunk to cause a hair root to be moved upward, and as a result, hair falls out, but old hair falls out, and new hair grows in the same position. Therefore, falling-out and growth are repeated with hair cycle in a lifetime.

A state in which the hair is not present in place where the hair should be present is referred to as alopecia, and examples of a cause of alopecia may include deterioration of functions of the hair follicles, deterioration of physiological functions of the scalp, local blood flow disturbance due to scalp tension, malnutrition, stress, adverse effect by a drug, genetic factors, chemicals, and diseases such as leukemia, tuberculosis, malignant lymphoma, and the like. In addition to the above-mentioned functions, since severe alopecia may also cause problems in social life, and a patient with alopecia may be psychologically depressed, alopecia may have a severe influence on quality of life. Therefore, it is very important to treat alopecia in view of quality of life Currently, as a most frequently used method for treating alopecia, a hair transplantation surgery method of transplanting patient's own hair and a drug treatment using minoxidil and Propecia® have been widely used. Minoxidil dilates the blood vessels to increase nutrient supply to hair follicles and have a potassium channel opening effect, or the like, to induce hair growth, and Propecia® has a dihydrotestosterone (DHT) formation inhibition effect to induce hair growth. However, in the cases of these drugs, at the time of treatment, both them have a hair growth effect, but when the treatment is discontinued, hair falls out again, and these drugs have a large effect in view of alopecia prevention rather than hair growth. Further, in the case of Propecia®, a side effect such as sexual dysfunction, birth defects in a woman, or the like, may occur. Recently, gene therapy performed by a method of delivering genes associated with alopecia to the follicles or inhibiting gene expression has been developed, but therapeutic efficacy and safety are uncertain, and treatment cost is expensive, such that it is not easy to clinically apply gene therapy.

Meanwhile, recently, a method of treating alopecia using stem cells, or the like, has been conducted. Currently, in most cases, as the method of treating alopecia using the stem cells, a method of directly injecting the stem cells in an alopecia or hairless site to induce differentiation into follicular cells has been used. However, this method has disadvantages in that treatment is impossible without using autologuous stem cells, a therapeutic effect is not continuously maintained, and a long time and high cost are consumed. In order to solve these problems, a method of treating alopecia using a culture solution produced at the time of culturing stem cells instead of the stem cells has been conducted, but efficiency enough to be commercialized has not yet been obtained.

DISCLOSURE

Technical Problem

An object of the present invention is to provide a hair growth-promoting composition capable of having an excellent hair growth-promoting effect and significantly simply delivering active ingredients to a human body to thereby have a high application value.

Technical Solution

According to an exemplary embodiment in the present invention, a hair growth-promoting composition contains: 100 parts by weight of a stem cell culture solution obtained from a culture medium of mesenchymal stem cells which have been subcultured two or more times; 100 to 300 parts by weight of a solvent; 0.001 to 0.1 parts by weight of zinc; 5 to 50 parts by weight of a panthenol based compound; and 0.0001 to 0.1 parts by weight of a water-soluble vitamin.

The hair growth-promoting composition may be a hair growth-promoting composition sprayed or applied on the scalp to promote hair growth. The composition may be sprayed (nebulized) or applied on the scalp to the human body, thereby promoting hair growth.

The stem cell culture solution may be a stem cell culture solution obtained from a culture medium subjected to a process including: (a) culturing the mesenchymal stem cells; and (b) three-dimensionally culturing the mesenchymal stem cells which have been subcultured two or more times together with a biocompatible scaffold in a serum-free medium.

The mesenchymal stem cells may be human adipose-derived stem cells.

The stem cell culture solution may contain vascular endothelial growth factor (VEGF), hepatocyte growth factor (HGF), fibroblast growth factor (FGF), transforming growth factor beta1 (TFG-β1), and epidermal growth factor (EGF) as growth factors, and contain collagen, fibronectin, laminin, and hyaluronic acid as extracellular matrix proteins.

As an example of the panthenol based compound, D-panthenol may be used, and as an example of the water-soluble vitamin, D-biotin may be used.

Advantageous Effects

A hair growth-promoting composition according to the present invention uses a culture solution, which is a by-product obtained by culturing stem cells, such that it is possible to promote economical efficiency in culturing the stem cells.

Most importantly, the hair growth-promoting composition according to the present invention may have an excellent hair growth-promoting effect, and excellent hair growth effect may be exhibited only by applying the composition for about several months.

Meanwhile, active ingredients may be delivered only by simply spraying, nebulizing, or applying the hair growth-promoting composition on the scalp or hair, such that a hair growth procedure may be significantly simplified.

DESCRIPTION OF DRAWINGS

FIG. 1 is photographs illustrating changes in hair with the passage of time after treating a patient with alopecia using a hair growth-promoting composition according to an exemplary embodiment of the present invention.

BEST MODE

Hereinafter, a hair growth-promoting composition according to an exemplary embodiment in the present disclosure will be described in detail.

The hair growth-promoting composition contains a stem cell culture solution obtained from a culture medium of mesenchymal stem cells which have been subcultured two or more times. The stem cell culture solution contains metabolites formed during culturing the stem cells in addition to the culture medium containing various additives.

In detail, a process of obtaining the stem cell culture solution may include: (a) culturing the mesenchymal stem cells; (b) collecting the mesenchymal stem cells which have been subcultured two or more times and three-dimensionally culturing the collected mesenchymal stem cells together with a biocompatible scaffold in a serum-free medium; and (c) collecting a culture medium.

Here, in (a) the culturing of the mesenchymal stem cells, it is preferable that the mesenchymal stem cells are cultured in a matrix medium and an expansion medium and then subcultured, and in (b) the three-dimensionally culturing the mesenchymal stem cells, it is preferable to obtain the stem cell culture solution at least three times while changing the medium every 3 days. Further, at least one of basic fibroblast growth factor (bFGF) and epidermal growth factor (EGF) may be added to the serum-free medium to perform the culturing.

In addition, the biocompatible scaffold, which is a cell support having a cell adhesive surface, may be a natural or synthetic polymer. Examples of the biocompatible scaffold include alginate, proteins, collagen, fibrin, hyaluronic acid, cellulose, poly(alpha-hydroxy acid) based polymers, poly (vinyl alcohol), polyanhydride, and the like.

A mesenchymal stem cell culture solution composition according to the present invention for achieving another object of the present invention is prepared by the method described above, such that the mesenchymal stem cell culture solution composition contains large amounts of growth factors and cytokines, and particularly contains high contents of VEGF and EGF. Preferably, contents of VEGF and EGF contained in the mesenchymal stem cell culture solution composition according to the present invention are equal to or higher than 4 times a content of VEGF and 17 times a content of EGG in a culture solution composition according to the related art, respectively.

The hair growth-promoting composition according to the present invention contains the stem cell culture solution containing large amounts of bioactive materials obtained by effectively culturing the mesenchymal stem cells in the serum-free medium as an ingredient. The mesenchymal stem cells used in the culturing may be obtained from the bone marrow, the cord blood, the adipose tissue, or the like. Particularly, adipose-derived stem cells have advantages in that it is relatively easy to approach the adipose-derived stem cells, the adipose-derivative stem cells may be simply collected, and a large amount of the adipose-derivative stem cells may be obtained from an individual.

According to the present invention, a large amount of mesenchymal stem cells may be effectively obtained within a short time by suitably using the matrix medium and the expansion medium in the culturing the mesenchymal stem cells. Further, in the method according to the present invention, the cells may be stably maintained for a long period of time by performing three-dimensional culturing using the biocompatible scaffold in the serum-free medium during a process of obtaining the culture solution, thereby making it possible to produce a large amount of cell culture solution. As described above, the stem cell culture solution produced by the method according to the present invention is characterized in that contents of the growth factors such as VEGF and EGF are significantly high as compared to a culture solution produced by two-dimensional culturing, which is a cell culturing method according to the related art. Since the mesenchymal stem cells are obtained from the human bone marrow, adipose tissue, cord blood, or the like, an amount of the human bone marrow, adipose tissue, cord blood, or the like, capable of being collected is small, and thus, the mesenchymal stem cells obtained from the above-mentioned tissue is also restricted. In order to use the stem cell culture solution for clinical purpose, it is preferable that a large amount of stem cell culture solution is obtained from a restrictive number of cells and contents of bioactive materials contained in the culture solution are high.

Generally, in order to culture and maintain mesenchymal stem cells, bovine-derived serum is required, but in order to use a cell culture solution for clinical purpose, it is preferable that the bovine-derived serum is not contained in the culture solution. In the case in which the bovine-derived serum is not contained in the culture medium of the mesenchymal stem cells, it is difficult to stably maintain the cells.

The present invention provides a method capable of stably culturing the mesenchymal stem cells in the serum-free medium in which the bovine-derived serum is not contained. The culture solution obtained by the method as described above contains significantly high contents of the growth factors as compared to a culture solution produced by an existing method. For example, a content of vascular endothelial growth factor (VEGF) contained in the stem cell culture solution obtained by the culturing method according to the present invention is increased by about 4 times as compared to the culturing method according to the related art, such that the stem cell culture solution may provide a significantly improved effect, and thus, the stem cell culture solution may be significantly utilized in view of clinical application.

In the case of three-dimensionally culturing stem cells together with a biocompatible scaffold such as fibrin glue according to the method in the present invention, since the stem cells may be cultured in a bottle having a simple shape without using a plate generally used for culturing cells, economical efficiency is significantly high, and a large amount of culture solution may be easily obtained. Further, in the two-dimensional culturing, since the number of cells is restricted depending on a size of a cell culture surface, contents of bioactive materials secreted from the stem cells are also restricted, but in the case of performing the three-dimensional culturing according to the present invention, since it is possible to adjust the number of cells, it is possible to increase concentrations of the bioactive materials in the culture solution if necessary.

Generally, in the case of plate-culturing the mesenchymal stem cells in the serum-free medium, the mesenchymal stem cells are not stably maintained, but are detached from the cell culture surface to die. According to the present invention, the mesenchymal stem cells having a property of attaching to something to grow may be stably maintained in a three-dimensional scaffold by culturing the mesenchymal stem cells together with the biocompatible scaffold. In the case of using fibrin glue as an example of the biocompatible scaffold, a survival rate of the mesenchymal stem cells was at least 80% for 14 days, and a high content of VEGF was continuously secreted as compared to the two-dimensional culturing.

Further, with the method according to the present invention, stability of the cells and the contents of the growth factors secreted in the culture solution may be increased in the case of adding basic fibroblast growth factor (bFGF) and/or epidermal growth factor (EGF) to the serum-free medium to performing the culturing.

In the present specification, the term "mesenchymal stem cells" means cells capable of having self-proliferation ability and multipotency and expressing cell phenotypes of CD73+, CD90+, CD105+, CD14−, CD20−, CD34−, and CD45−, and the mesenchymal stem cells may be isolated from the bone marrow, the adipose tissue, the cord blood, or the like, but are not limited thereto. However, in a quantitative point of view of the active ingredients of the culture solution, adipose-derived stem cells may be preferable.

In the present specification, the term "bioactive material" collectively means cytokines, cell growth factors, and the like, which may affect functions of cells or human bodies. The term "stem cell culture solution" means a cell culture supernatant obtained by culturing the stem cells. The stem cell culture solution contains various bioactive materials secreted from the cells during the process of culturing the stem cells.

The term "biocompatible scaffold" means a support which may have an affinity to cells and be made of a material having a "cell adhesive surface" and to which cells may be three-dimensionally attached and cultured. An example of a nature-derived support may include alginate, proteins, collagen, fibrin, hyaluronic acid, cellulose, or the like, but is not limited thereto. An example of a synthetic polymer may include poly(alpha-hydroxy acid) based polymer, poly(vinyl alcohol), polyanhydride, or the like, but is not limited thereto.

In the present invention, the three-dimensional culturing may be performed using the biocompatible scaffold such as fibrin glue. With the method according to the present invention, contents of human-derived growth factors, particularly, VEGF and EGF may be significantly increased by three-dimensionally culturing the mesenchymal stem cells together with fibrin glue at the time of culturing the mesenchymal stem cells in the serum-free medium. That is, in the two-dimensional culturing, there is a limitation in increasing the contents of VEGF, and the like, contained in the culture solution even under a hypoxic condition, and the stem cell culture solution may be obtained only once. However, in the three-dimensional culturing, since the stem cells are stably maintained and continuously secret high concentrations of the cell growth factors, it is possible to obtain the culture medium at least three times while changing the culture medium every three days. Further, with the three-dimensional culturing method according to the present invention, since the culturing may be performed in a bottle unlike the plate culturing according to the related art, the stem cell culture solution is possible.

The mesenchymal stem cells may be cultured through the following processes, and a medium used for culturing the cells is not limited thereto.

(1) Culturing of Mesenchymal Stem Cells

After suspending mesenchymal stem cells obtained from the corresponding tissue in a matrix medium and inoculating the suspended mesenchymal stem cells into a culture vessel in a concentration of 10,000 to 40,000 cells/cm$^2$, the mesenchymal stem cells were cultured. The matrix medium was Dulbecco's modified eagle medium (DMEM) or Dulbecco's modified eagle medium/Ham's F-12 nutrient broth (DMEM/F12) medium containing bovine serum, and the culturing was performed for about 24 hours.

(2) Culturing in Expansion Media

After removing the matrix medium, the cultured mesenchymal stem cells were cultured in an expansion medium to proliferate adherent cells. The expansion medium was a DMEM or DMEM/F12 medium containing bovine serum (10%), epidermal growth factor (EGF, 0.1~100 ng/ml), and/or basic fibroblast growth factor (bFGF, 0.1~100 ng/ml) and served to rapidly proliferate the adherent mesenchymal stem cells to increase an amount of cells within a short time on a large scale.

(3) Sub-Culturing

When cells occupied 80 to 90% of a bottom of the culture vessel, the expansion medium was removed, and the cells were detached from the culture vessel by trypsin treatment. For subculturing, the cells were diluted at 1:3 to 1:4, and the diluted cells were cultured together with the expansion medium in a novel culture vessel. Additional subculturing may be performed by the above-mentioned method.

(4) Culturing with Biocompatible Scaffold

The cultured cells were washed with phosphate-buffered saline (PBS) three times or more to remove fetal bovine serum (FBS), and the resultant cells were cultured in a serum-free medium in a state in which the cells were attached to a biocompatible scaffold. Since cell culturing in the scaffold does not require a general cell culture vessel, the cells may be cultured in a sterilized bottle or culture bag on a large scale, which has an advantage in that the cells may be conveniently cultured with a lower cost.

The stem cell culture solution may contain vascular endothelial growth factor (VEGF), hepatocyte growth factor (HGF), fibroblast growth factor (FGF), transforming growth factor beta1 (TFG-β1), and epidermal growth factor (EGF) as growth factors, and contain collagen, fibronectin, laminin, and hyaluronic acid as extracellular matrix proteins.

The hair growth-promoting composition may contain 0.001 to 0.1 parts by weight of zinc based on 100 parts by weight of the stem cell culture solution. Further, the hair growth-promoting composition may contain 5 to 50 parts by weight of a panthenol based compound based on 100 parts by weight of the stem cell culture solution. As an example of the panthenol based compound, there is D-panthenol, or the like, and other panthenol derivatives, or the like, may be used.

The hair growth-promoting composition may contain 0.0001 to 0.1 parts by weight of a water-soluble vitamin based on 100 parts by weight of the stem cell culture solution. As the water-soluble vitamin, D-biotin, or the like, may be used, and other water-soluble vitamins in various forms may be additionally used.

Each of the ingredients, that is, zinc, the panthenol based compound, the water-soluble vitamin, and the like, are mixed with the stem cell culture solution in an aqueous solution state. As a result, the hair growth-promoting composition contains an aqueous solvent, and 100 to 300 parts by weight of the aqueous solvent may be contained based on 100 parts by weigh to the stem cell culture solution. As the aqueous solvent, a water ingredient such as a saline solution, or the like, is preferable.

The hair growth-promoting composition may exhibit a hair growth effect only by nebulizing or spraying the hair growth-promoting composition on the scalp or uniformly applying the hair growth-promoting composition on the scalp. That is, since there is no need to administer the hair growth-promoting composition to the scalp by injection, alopecia treatment may be simplified.

Hereinafter, results obtained by performing a test for proving the hair growth effect of the hair growth-promoting composition according to the exemplary embodiment of the present invention will be described.

Example: Preparation of Hair Growth-Promoting Composition for Test

A hair growth-promoting composition having the ingredient composition illustrated in the following Table 1 was prepared.

TABLE 1

| | Ingredient | | | |
|---|---|---|---|---|
| | Stem Cell Culture solution | Zn Aqueous Solution | D-Panthenol | D-biotin |
| Volume | 2 cc | 1 cc (1 mg) | 1 cc (250 mg) | 1 cc (0.12 mg) |

Evaluation of Hair Growth Property of Hair Growth-Promoting Composition for Test FIG. 1 is photographs illustrating changes in hair with the passage of time after treating a patient with alopecia using a hair growth-promoting composition according to an exemplary embodiment of the present invention.

A target patient was treated with the hair growth-promoting composition prepared in the Example described above once a week by spraying 7 cc of the hair growth-promoting composition.

Referring to FIG. 1, it may be confirmed that with the passage of time, hair growth clearly occurred as compared to a state before treatment. Particularly, it was confirmed that effective hair growth may occur by treatment only for 2 months. The effect may be somewhat changed depending on a type of patient with alopecia, but it was judged that excellent effect and efficacy of the hair growth-promoting composition was sufficiently confirmed.

The invention claimed is:

1. A composition for spraying or applying on a scalp to promote hair growth, the composition comprising:
   100 parts by weight of a stem cell culture solution obtained from a culture medium subjected to a process including separately adding a growth factor bFGF or EGF to a serum-free medium which does not contain bovine-derived serum and culturing human adipose-derived mesenchymal stem cells which have been subcultured two or more times in the serum-free medium;
   100 to 300 parts by weight of a solvent based on the 100 parts by weight of the stem cell culture solution;
   0.001 to 0.1 parts by weight of zinc based on the 100 parts by weight of the stem cell culture solution;
   5 to 50 parts by weight of D-panthenol based on the 100 parts by weight of the stem cell culture solution; and
   0.0001 to 0.1 parts by weight of D-biotin based on the 100 parts by weight of the stem cell culture solution.

2. The composition of claim 1, wherein the stem cell culture solution is obtained from the culture medium subjected to the process further including:
   three-dimensionally culturing the human adipose-derived mesenchymal stem cells which have been subcultured two or more times together with a biocompatible scaffold in the serum-free medium.

3. The composition of claim 1, wherein the stem cell culture solution contains vascular endothelial growth factor (VEGF), hepatocyte growth factor (HGF), fibroblast growth factor (FGF), transforming growth factor beta1 (TGF-β1), and epidermal growth factor (EGF) as growth factors, and contains collagen, fibronectin, laminin, and hyaluronic acid as extracellular matrix proteins.

* * * * *